(12) United States Patent
Susaki et al.

(10) Patent No.: US 10,267,714 B2
(45) Date of Patent: Apr. 23, 2019

(54) COMPOSITION FOR PREPARING BIOMATERIAL WITH EXCELLENT LIGHT-TRANSMITTING PROPERTY, AND USE THEREOF

(71) Applicant: RIKEN, Wako-shi, Saitama (JP)

(72) Inventors: Etsuo Susaki, Wako (JP); Hiroki Ueda, Wako (JP); Kazuki Tainaka, Wako (JP)

(73) Assignee: RIKEN, Wako-Shi, Saitama (JP)

( * ) Notice: Subject to any disclaimer, the term of this patent is extended or adjusted under 35 U.S.C. 154(b) by 0 days.

(21) Appl. No.: 14/911,778

(22) PCT Filed: Aug. 5, 2014

(86) PCT No.: PCT/JP2014/070618
§ 371 (c)(1),
(2) Date: Feb. 12, 2016

(87) PCT Pub. No.: WO2015/022883
PCT Pub. Date: Feb. 19, 2015

(65) Prior Publication Data
US 2016/0266016 A1   Sep. 15, 2016

(30) Foreign Application Priority Data

Aug. 14, 2013 (JP) .................................. 2013-168705

(51) Int. Cl.
*G01N 1/30* (2006.01)
(52) U.S. Cl.
CPC ...................................... *G01N 1/30* (2013.01)
(58) Field of Classification Search
CPC ....................................................... G01N 1/30
See application file for complete search history.

(56) References Cited

U.S. PATENT DOCUMENTS

| | | | |
|---|---|---|---|
| 2,029,525 A | 2/1936 | Montclair | |
| 4,493,821 A | 1/1985 | Harrison | |
| 4,578,282 A | 3/1986 | Harrison | |
| 4,981,610 A | 1/1991 | Linden et al. | |
| 5,057,435 A | 10/1991 | Denney | |
| 5,530,100 A * | 6/1996 | Darling ................ | C07K 14/755 435/69.6 |

(Continued)

FOREIGN PATENT DOCUMENTS

| | | |
|---|---|---|
| CN | 1068653 | 2/1993 |
| CN | 1337462 | 2/2002 |

(Continued)

OTHER PUBLICATIONS

International preliminary report on patentability of PCT/JP2013/073891 dated Apr. 28, 2015.

(Continued)

*Primary Examiner* — Shafiqul Haq
(74) *Attorney, Agent, or Firm* — Kristina Castellano; Castellano PLLC

(57) ABSTRACT

The present invention provides an aminoalcohol together with, as necessary, at least one selected from the group consisting of: at least one compound selected from the group consisting of urea and a urea derivative; a nonionic detergent; and sucrose to provide a biological material having an excellent light-transmitting property. The present invention provides a technique that allows a high-throughput observation of gene expression/localization or cell morphology in tissue at an whole-tissue level.

6 Claims, 4 Drawing Sheets

(56) References Cited

U.S. PATENT DOCUMENTS

| | | | |
|---|---|---|---|
| 5,612,028 | A | 3/1997 | Sackier et al. |
| 5,624,682 | A * | 4/1997 | Dondi .................. A61K 9/4858 424/451 |
| 6,072,086 | A | 6/2000 | James et al. |
| 6,207,408 | B1 | 3/2001 | Essenfeld et al. |
| 6,232,092 | B1 | 5/2001 | Rogers |
| 6,319,683 | B1 | 11/2001 | James et al. |
| 6,462,071 | B1 | 10/2002 | Castillejos |
| 6,703,242 | B1 | 3/2004 | Senatorov |
| 6,891,023 | B1 | 5/2005 | de Acosta Del Rio et al. |
| 7,008,960 | B1 | 3/2006 | Castillejos |
| 8,383,403 | B2 | 2/2013 | Wang et al. |
| 2001/0000487 | A1 | 4/2001 | Essenfeld et al. |
| 2001/0031482 | A1 | 10/2001 | James et al. |
| 2001/0043884 | A1 | 11/2001 | Essenfeld et al. |
| 2001/0051365 | A1 | 12/2001 | Morales et al. |
| 2002/0077697 | A1 | 6/2002 | Ranieri et al. |
| 2003/0199574 | A1 | 10/2003 | Karageozian et al. |
| 2004/0004075 | A1 | 1/2004 | Morales et al. |
| 2004/0043082 | A1 | 3/2004 | Karageozian et al. |
| 2005/0137124 | A1 | 6/2005 | Castillejos |
| 2005/0142142 | A1 * | 6/2005 | Burrows ............ A61K 39/0008 424/185.1 |
| 2006/0110720 | A1 | 5/2006 | Fujisato et al. |
| 2007/0105950 | A1 | 5/2007 | Karageozioan et al. |
| 2008/0125580 | A1 | 5/2008 | Pizarro et al. |
| 2008/0153127 | A1 | 6/2008 | Morales et al. |
| 2008/0160542 | A1 | 7/2008 | Yasuda et al. |
| 2008/0280980 | A1 | 11/2008 | Van Dyke |
| 2009/0162437 | A1 | 6/2009 | Horii et al. |
| 2009/0191138 | A1 | 7/2009 | Dechow |
| 2010/0285560 | A1 | 11/2010 | Wang et al. |
| 2011/0123979 | A1 | 5/2011 | Salmon et al. |
| 2011/0294990 | A1 | 12/2011 | Pizarro et al. |
| 2012/0196937 | A1 | 8/2012 | Karageozian et al. |
| 2013/0123474 | A1 | 5/2013 | Pizarro et al. |
| 2013/0188038 | A1 | 7/2013 | Tanimoto et al. |
| 2014/0087419 | A1 | 3/2014 | Miyawaki et al. |

FOREIGN PATENT DOCUMENTS

| | | |
|---|---|---|
| CN | 101042317 | 9/2007 |
| CN | 101506222 | 8/2009 |
| CN | 101871855 | 10/2010 |
| CN | 103492862 A | 1/2014 |
| EP | 0246978 | 11/1987 |
| EP | 0333328 | 9/1989 |
| EP | 2133069 A1 | 12/2009 |
| JP | 3-167472 A | 7/1991 |
| JP | 6-080502 A | 3/1994 |
| JP | 6-505560 | 6/1994 |
| JP | 2000-509146 | 7/2000 |
| JP | 2003-514831 | 4/2003 |
| JP | 2003-517601 | 5/2003 |
| JP | 2004-97552 | 4/2004 |
| JP | 2005-522464 | 7/2005 |
| JP | 2007070494 A * | 3/2007 |
| JP | 2008-161138 | 7/2008 |
| JP | 2009-221252 A | 10/2009 |
| JP | 2010-504972 | 2/2010 |
| JP | 2011-012226 A | 1/2011 |
| WO | 2007-061783 | 5/2007 |
| WO | 2008/008975 A2 | 1/2008 |
| WO | 2008/088403 | 7/2008 |
| WO | 2010/007350 | 1/2010 |
| WO | 2011/111876 A1 | 9/2011 |

OTHER PUBLICATIONS

International Search Report of PCT/JP2013/073891 dated Dec. 10, 2013.
Mahara, A., et al., Surface modification procedure of acellular vascular grafts with the cell binding peptide, Polymer Preprints, Japan, 2011, vol. 60, No. 1, p. 1751.
Mahara, A., et al., Small-caliber longbypass graft by using decellularized ostrich carotid artery and peptide modification, Polymer Preprints, Japan, May 14, 2013, vol. 62, No. 1, p. 1773.
Tetsuji Yamaoka et al., "Acellular vascular grafts for regenerative medicine", Recent Advances in Cardiovascular Disease, Nov. 30, 2012 (Nov. 30, 2012), vol. 33, No. 1, pp. 56 to 63.
Mahara, A., et al., Small-caliber decellularized long-bypass graft by using peptide modification, Polymer Preprints, Japan, Sep. 5, 2012, vol. 61, No. 2, pp. 4761-4762.
Haruka Yamaguchi et al., "Noninvasive Evaluation of Calcification in Acellular Blood Vessels", The 31st Annual Meeting of the Japanese Society for Biomaterials Compilation of abstracts of papers p. 374.
Funamoto, S., et al., The use of highhydrostatic pressure treatment to decellularize blood vessels, Biomaterials, 2010, vol. 31, No. 13, pp. 3590-3595.
Sasaki, S., et al., In vivo evaluation of a novel scaffold for artificial corneas prepared by using ultrahigh hydrostatic pressure to decellularize porcine corneas, Molecular Vision, 2009, vol. 15, pp. 2022-2028.
Tetsuji Yamaoka et al., "Luminal surface modification and the patency of smalldiameter acellular vascular grafts", ABML 2011 (Assistive Technology, Bio Medical Engineering and Life Support) Compilation of theses pp. OS2-4-1 and OS2-4-2.
Atsushi Mahara et al., "Evaluation of patency of acellular small diameter vascular graft which is surface-modified by endothelial cell adhesive peptide", Regenerative Medicine, Extra issue the Japanese Society for Regenerative Medicine magazine vol. 11, Suppl. 2012 Program/Abstract of the 11th Congress of Japanese Society for Regenerative Medicine p. 174, O-10-5.
Office Action for U.S. Appl. No. 13/583,548 dated Mar. 29, 2017.
EP search report for 14836073.8, dated Mar. 23, 2017.
EP Office Action for 12788804.8, dated Feb. 17, 2017.
Office Action for U.S. Appl. No. 14/113,639, dated Jan. 23, 2017.
Office Action for U.S. Appl. No. 14/118,150, dated Sep. 2, 2016.
Office Action for U.S. Appl. No. 14/118,150, dated Apr. 14, 2016.
Office Action for CN 201280023902.6, dated Apr. 22, 2015.
European Seach report of corresponding EP application No. 12788804.8 dated Dec. 1, 2014.
Khoudoli Guennadi A et al, "Optimisation of the two-dimensional gel eletrophoresis protocol using the Taguchi approach", Proteome Science, Biomed Central, London, GB, vol. 2, No. 1, Sep. 9, 2014.
Office Action for U.S. Appl. No. 13/583,548 dated Jun. 8, 2016.
Office Action for U.S. Appl. No. 14/113,639 dated May 9, 2016.
1 st Office Action for U.S. Appl. No. 13/583,548, dated Jun. 26, 2013.
Office Action for U.S. Appl. No. 13/583,548 dated Feb. 13, 2013.
3rd Office Action for U.S. Appl. No. 13/583,548 dated Aug. 27, 2015.
European Seach report of corresponding EP application No. 11753531.0 dated Mar. 24, 2015.
Office Action of Corresponding JP application No. 2012-556745 dated Mar. 31, 2015.
Jonathan H. Clarke et al. Distribution and Neuronal Expression of Phosphatidylinositol Phosphate Kinase II γ in the Mouse Brain, <The Journal of Comparative Neurology>vol. 517 p. 296-312, dated Dec. 31, 2009.
Bondos et al. (Analytical Biochemistry, vol. 316, p. 223-231, 2003).
McCormick et al. (Proceedings of the National Academy of Sciences, vol. 97, No. 2, p. 668-673, dated 2000).
2ndOA for U.S. Appl. No. 13/583,548 dated May 27, 2014.
Office Action for CN 201180013354.4 dated Apr. 28, 2014.
Final Office Action for U.S. Appl. No. 13/583,548 dated Jan. 13, 2014.
Shi et al. (Journal of Histochemistry & Cytochemistry, vol. 41, p. 1599-1604, dated 1993).
Jansen et al., The Journal of Biomedical Optics vol. 11(4) 041119 Jul./Aug. 2006.
Seabold et al., Journal of Visualized Experiments, vol. 41, p. 2081-2085, 2010.

(56) References Cited

OTHER PUBLICATIONS

H. Honma, "A Study of the Vascular Network of Sciatic Nerves in Experimental Chronic Diabetic Rat", Journal of St. Marianna University School of Medicine Hospital, vol. 27, No. 4, Aug. 1, 1999, pp. 339-347.
A. Kyuma, "Histochemical Studies on Glycoconjugates in the Salivary Gland Connective Tissues of Laboratory Animals", Journal of Nagoya City University Medical School, vol. 42, No. 2, May 1, 1991, pp. 183-208.
T. Sakagami et al., "Effects of treatment with urea upon the electron microscopic histochemical reactions of acidic glycoconjugates in fixed tissues", Connect Tissue, vol. 21, No. 2, Nov. 1989, pp. 37-38.
Geoffrey S. Baird et al., "Biochemistry, mutagenesis, and oligomerization of DsRed, a red fluorescent protein from coral", PNAS., vol. 97, No. 22, Oct. 24, 2000, pp. 11984-11989.
S. Karasawa et al., "A Green-emitting Fluorescent Protein from Galaxeidae Coral and Its Monomeric Version for Use in Fluorescent Labeling", The Journal of Biological Chemistry, vol. 278, No. 36, 2003, pp. 34167-34171.
T. Nagai et al., "A Variant of yellow fluorescent protein with fast and efficient maturation for cell-biological applications" Nature Biotechnology, vol. 20, Jan. 2002, pp. 87-90.
G. Zhang et al., "An Enhanced Green Fluorescent Protein Allows Sensitive Detection of Gene Transfer in Mammalian Cells", Biochemical and Biophysical Research Communications, vol. 227, No. 3, 1996, pp. 707-711.
Anna-Katerina Hadjantonakis et al., "Embryonic stem cells and mice expressing different GFP variants for multiple non-invasive reporter usage within a single animal", BMC Biotechnology. 2:11, Jun. 11, 2002, pp. 1-9.
William F. Scherer et al., "Studies on the propagation in Vitro of Poliomyelitis Viruses", J. Exp. Med. vol. 97, No. 5, May 1, 1953, pp. 695-710.
A. Sakaue-Sawano et al., "Visualizing Spatiotemporal Dynamics of Multicellular Cell-Cycle Progression" Cell. vol. 132, No. 3, Feb. 8, 2008, pp. 487-498.
G. Feng et al., "Imaging Neuronal Subsets in Transgenic Mice Expressing Multiple Spectral Variants of GFP", Neuron, vol. 28, Oct. 2000, pp. 41-51.
Ann-Shyn Chiang et al., "Insect NMDA receptors mediate juvenile hormone biosynthesis", PNAS, vol. 99, No. 1, Jan. 8, 2002, pp. 37-42.
International Search Report dated Jun. 21, 2011, International Patent Application No. PCT/JP2011/056502, dated Jun. 21, 2011.
Office Action for CN201180013354.4, dated Sep. 29, 2015.
1st Office Action for U.S. Appl. No. 14/113,639 dated Nov. 4, 2015.
Caetano-Anolles (1997). Resolving DNA Amplification Products Using Polyacrylamide Gel Electrophoresis and Silver Staining, Chapter. XIII in Fingerprinting Methods based on Arbitrarily Primed PCR, ISBN (online): 978-3-642-60441-6, p. 119-134.
Hurkman et al. (1986). Solubilization of Plant Membrane Proteins for Analysis by Two-Dimensional Gel Electrophoresis . . . , Plant Physiology, v81, p. 802-806.
Hamnes et al. (1967). An Investigation of Water-Urea and Water-Urea-Polyethylene Glycol Interactions. JAGS, v89(2), p. 442-446.
Das Gupta et al. (1989). Effects of urea and nonionic surfactant on the micellization and counterion binding properties of cetylmethyl ammonium bromide and sodium dodecyl sulfate., Colloid & Polymer Science, v267, p. 246-254.
Office Action for U.S. Appl. No. 14/113,639 dated Jul. 21, 2015.
Shaw and Chambers(1721) "A New Method of Chemistry . . . ", p. 193 (pre-1941), roman numeral date 1727.
Office Action for 201280020354.1 dated Mar. 3, 2015.
European Search Report for 12777671.4 dated Aug. 19, 2014.
Office Action for U.S. Appl. No. 13/583,548, dated Aug. 17, 2017.
Crapo et al. An overview of tissue and whole organ decellularization processes. Biomaterials (epub Feb. 5, 2011), v32, p. 3233-3243, available online Feb. 5, 2011.
Office Action for U.S. Appl. No. 14/113,639 dated Jul. 11, 2017.
Advisory Action in related U.S. Appl. No. 14/113,639, dated Nov. 16, 2017.
Chen, et al., "Hoxb5 marks long-term haematopoietic stem cells and reveals a homogenous perivascular niche", Nature, vol. 530, Feb. 11, 2016.
Susaki, et al., "Whole-Brain Imaging with Single-Cell Resolution Using Chemical Cocktails and Computational Analysis", Cell 157, 726-739, Apr. 24, 2014.
Tainaka, et al., "Whole-Brain Imaging with Single-Cell Resolution by Tissue Decolorization", Cell 159, 911-924, Nov. 6, 2014.
Office Action in co-pending U.S. Appl. No. 13/583,548, dated Jun. 25, 2018.
1st Office Action in U.S. Appl. No. 14/113,639 dated May 29, 2018.
Office Action for JP application 2015-531767, dated Jul. 24, 2018 and translation thereof.
Office Action in U.S. Appl. No. 13/583,548 dated Feb. 8, 2019.

* cited by examiner

FIG. 2
(a)
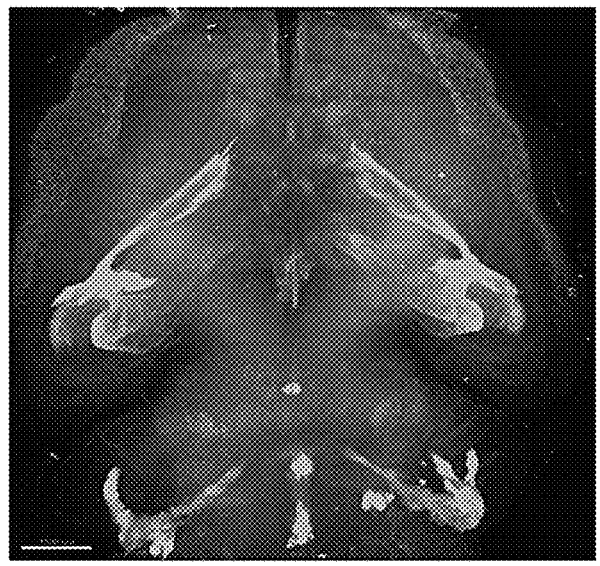
(b)
(d)
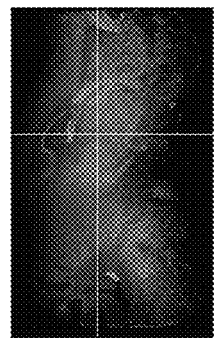
(c)
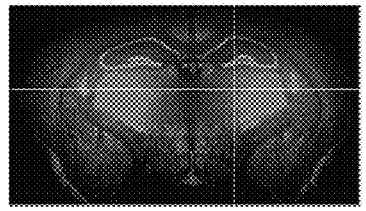

FIG. 3
(a)
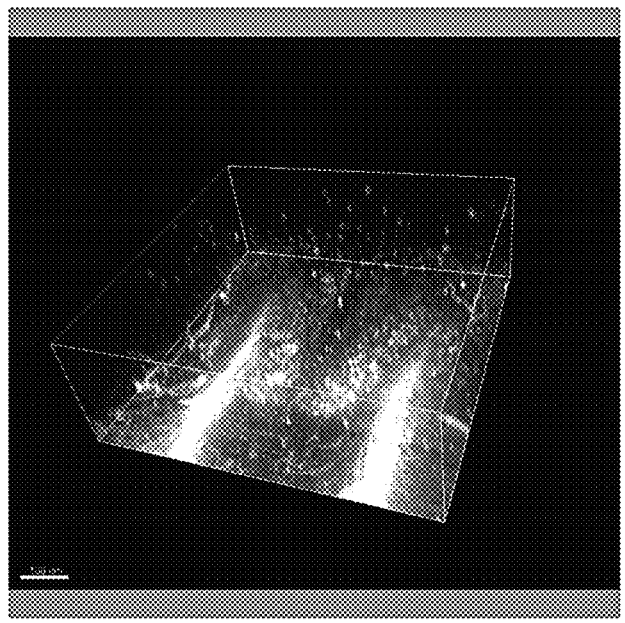
(b)
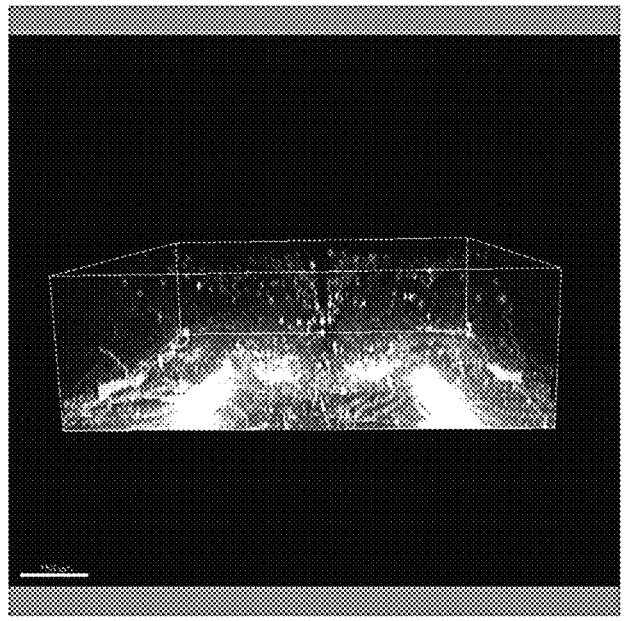

COMPOSITION FOR PREPARING BIOMATERIAL WITH EXCELLENT LIGHT-TRANSMITTING PROPERTY, AND USE THEREOF

CLAIM FOR PRIORITY

This application is a U.S. National Stage Application of PCT/JP2014/070618 filed on Aug. 5, 2014, which claims priority to Japanese Application 2013-168705 filed on Aug. 14, 2013, the contents of both of which are incorporated herein by reference.

TECHNICAL FIELD

The present invention relates to a composition for preparing a biological material having an excellent light-transmitting property and to use of the composition.

BACKGROUND ART

For high-level observations of gene expression within tissue, intracellular localization, and cell morphology, a pretreatment (clearing treatment) for increasing the light-transmitting property of tissue has been performed with use of a clearing reagent in recent years. Various clearing reagents and pretreatment methods have thus been developed.

Non Patent Literatures 1 and 2 each disclose a clearing treatment technique involving use of benzylbenzoate/benzylalcohol (BABB method). The BABB method is a classic tissue clearing method involving use of an organic solvent, and has been applied as a method for preparing a cleared sample to be observed through a light-sheet macro-zoom microscope (see, for example, Non Patent Literature 3).

Non Patent Literature 4 discloses a technique (SeeDB method) of adjusting the refractive index with use of fructose. The SeeDB method is primarily intended to minimize a change caused to biological tissue during the treatment, and thus the biological tissue substantially completely maintains the molecular-level structure, membrane structure, axon shape, and the like. The SeeDB method, in a case where it uses a two-photon microscope and an optimized lens, allows observation at a level of the whole brain.

Non Patent Literature 5 discloses a clearing technique (CLARITY method) based on a physicochemical method involving use of an electrophoresis apparatus. The CLARITY method uses an electrophoresis apparatus to physicochemically treat brain tissue packed with use of an acrylamide polymer for removal of lipid components to make the brain tissue transparent. The CLARITY method allows high-level clearing in approximately two weeks in a state where the molecular-level structure of tissue is maintained. The CLARITY method is applicable to both (i) fluorescent protein labelling and (ii) immunostaining.

Non Patent Literature 6 discloses a technique (Scale method) that uses a water-soluble reagent to successfully minimize quenching of fluorescence signals.

CITATION LIST

Non-Patent Literature

Non Patent Literature 1
Hans-Ulrich Dodt et al., "Ultramicroscopy: three-dimensional visualization of neuronal networks in the whole mouse brain", Nature Methods, vol. 4, No. 4: 331-336 (2007)

Non Patent Literature 2
Klaus Becker et al., "Chemical Clearing and Dehydration of GFP Expressing Mouse Brains", PLoS ON E, vol. 7, issue 3: e33916 (2012)

Non Patent Literature 3
Philipp J. Keller et al., "Reconstruction of Zebrafish Early Embryonic Development by Scanned Light Sheet Microscopy", Science, vol. 322: 1065-1069 (2008)

Non Patent Literature 4
Meng-Tsen Ke et al., "SeeDB: a simple and morphology-preserving optical clearing agent for neuronal circuit reconstruction", advance online publication (published online 23 Jun. 2013)

Non Patent Literature 5
Kwanghun Chung et al., "Structural and molecular interrogation of intact biological systems", Nature, vol. 497: 332-339 (2013)

Non Patent Literature 6
Hiroshi Hama et al., "Scale: a chemical approach for fluorescence imaging and reconstruction of transparent mouse brain", Nature Neuroscience, vol. 14, No. 11: 1481-1490 (2011)

SUMMARY OF INVENTION

Technical Problem

The BABB method, described in each of Non Patent Literatures 1 and 2, allows high transparency for a cleared sample produced, but is problematic in that the fluorescence signals are quenched rapidly due to a dehydration process and an organic solvent treatment. Further, with the BABB method, it is difficult to perform immunostaining and a clearing treatment while maintaining three-dimensional tissue. In addition, since the BABB method uses an organic solvent, there is a safety concern.

The SeeDB method, described in Non Patent Literature 4, allows observation at a whole-brain level, but requires several days for scanning. Further, the SeeDB method assumes use of a two-photon microscope, and the transparency of tissue treated (adult brain in particular) is thus not high enough for observation through a light-sheet macro-zoom microscope.

The CLARITY method, described in Non Patent Literature 5, involves a complicated process and requires a dedicated device. The CLARITY method is thus not suited for multiple samples.

The Scale method, described in Non Patent Literature 6, does not allow tissue (adult brain in particular) to have transparency high enough for application of a light-sheet system. Further, the Scale method requires a period in weeks to months before completion of making tissue transparent.

The present invention has been accomplished to solve the above problems. It is an object of the present invention to provide a technique for a high-throughput observation of gene expression/localization or cell morphology in tissue at a whole-tissue level without use of an organic solvent.

Solution to Problem

In order to solve the above problems, the inventors of the present invention conducted diligent studies, and have thus discovered that a particular combination of particular compounds can increase the light-transmitting property of tissue to such a level that the tissue is adaptable for high-throughput three-dimensional imaging. The inventors have therefore completed the present invention.

Specifically, in order to prepare a biological material having an excellent light-transmitting property, a reagent composition according to the present invention includes an aminoalcohol. The reagent composition according to the present invention may further include at least one selected from the group consisting of: at least one compound selected from the group consisting of urea and a urea derivative; a nonionic detergent; and sucrose.

In order to prepare a biological material having an excellent light-transmitting property, a reagent kit according to the present invention is characterized by including: a first solution including: an aminoalcohol; at least one compound selected from the group consisting of urea and a urea derivative; and a nonionic detergent; and a second solution including: an aminoalcohol; at least one compound selected from the group consisting of urea and a urea derivative; and sucrose. In the reagent kit according to the present invention, the second solution may further include a nonionic detergent.

In order to produce the above reagent composition or reagent kit, a composition according to the present invention is characterized by including an aminoalcohol.

In order to produce the above reagent composition or reagent kit, a kit according to the present invention is characterized by including: an aminoalcohol; and at least one selected from the group consisting of at least one compound selected from the group consisting of urea and a urea derivative, a nonionic detergent, and sucrose.

A method according to the present invention for preparing a biological material having an excellent light-transmitting property is characterized by including a first permeating step of permeating into a biological material a first solution including: an aminoalcohol; at least one compound selected from the group consisting of urea and a urea derivative; and a nonionic detergent.

The above method may further include a second permeating step of permeating into the biological material a second solution including: an aminoalcohol; at least one compound selected from the group consisting of urea and a urea derivative; and sucrose. The second solution may further include a nonionic detergent.

A biological material according to the present invention is characterized by being prepared by the above method to have an excellent light-transmitting property.

An immunohistochemical assay according to the present invention is characterized by using a biological material prepared by any of the above methods.

A method according to the present invention for searching for a tissue site reactive with an autoantibody is characterized by using the above immunohistochemical assay.

A method according to the present invention for searching for an antigen against an autoantibody is characterized by using the above immunohistochemical assay.

A biochemical assay according to the present invention is characterized by using a biological material prepared by any of the above methods.

Advantageous Effects of Invention

The present invention is a technique based on a chemical treatment, and does not require employment of specialized equipment and a complicated manipulation. Further, the present invention uses a simple process to make it possible to make a biological material transparent at a level high enough for a high-throughput analysis of multiple samples.

BRIEF DESCRIPTION OF DRAWINGS

FIG. 2 is a figure according to an Example of the present invention which figure shows results of treating a whole mouse brain with use of the present invention and scanning the whole mouse brain.

FIG. 3 is a figure according to an Example of the present invention which figure shows results of a three-dimensional immunohistochemical assay for a whole mouse brain treated with use of the present invention.

DESCRIPTION OF EMBODIMENTS

Figure 1:
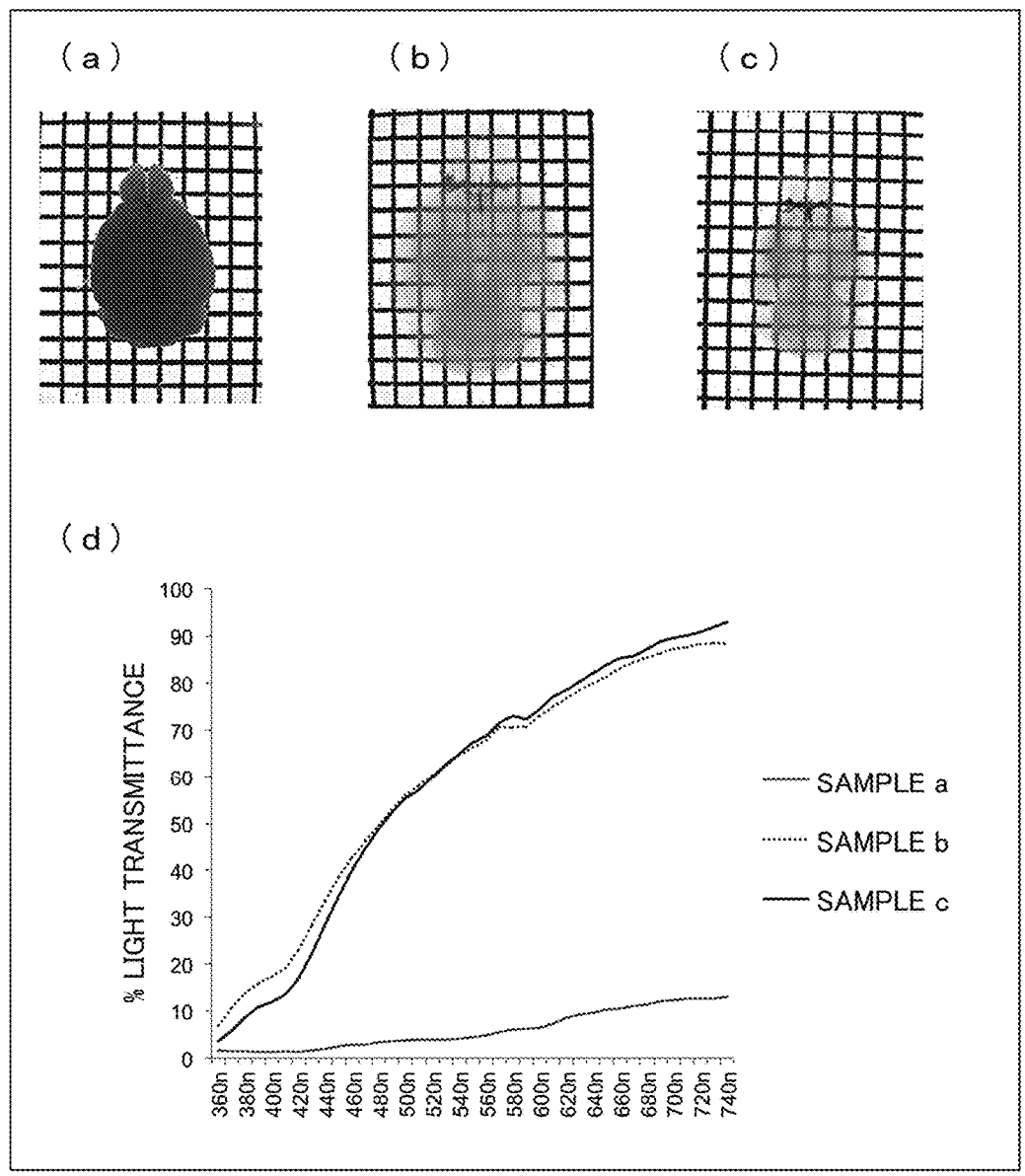
FIG. 1 is a figure according to an Example of the present invention which figure shows results of checking light-transmitting properties of whole mouse brains treated with use of the present invention.

The inventors of the present invention conducted large-scale screening based on a unique viewpoint, selected several kinds of aminoalcohols, nonionic detergents, and urea, and completed a first solution for achieving high-throughput tissue imaging. The inventors of the present invention further completed a second solution containing sucrose on the basis of another unique viewpoint. The inventors of the present invention have then confirmed that the above solutions provide effects superior to the effects produced by conventionally publicly known clearing reagents, and have discovered very particularly that the two solutions when used in combination produce excellent effects.

The following will describe an embodiment of the present invention in detail.

[1. Composition and Kit]

The present invention provides a reagent composition for preparing a biological material having an excellent light-transmitting property. A reagent composition according to the present invention is characterized by being a solution containing an aminoalcohol. A reagent composition according to the present invention may contain urea or a urea derivative. A reagent composition according to the present invention may be either a composition (hereinafter referred to as "first solution" or "first reagent") not containing sucrose or a composition (hereinafter referred to as "second solution" or "second reagent") further containing sucrose. In the former case, the reagent composition preferably further contains a nonionic detergent. In the latter case, the reagent composition may further contain a nonionic detergent.

The present invention also provides a reagent kit for preparing a biological material having an excellent light-transmitting property. A reagent kit according to the present invention is characterized by including: a first solution including: an aminoalcohol; urea or a urea derivative; and a nonionic detergent; and a second solution including: an aminoalcohol; urea or a urea derivative; and sucrose. The second solution may further include a nonionic detergent as necessary.

The present invention further provides a composition for producing a reagent composition for preparing a biological material having an excellent light-transmitting property. In this embodiment, a composition according to the present invention is characterized by including an aminoalcohol.

The present invention also provides a kit for producing a reagent composition for preparing a biological material having an excellent light-transmitting property. In this embodiment, a kit according to the present invention is characterized by including: an aminoalcohol; urea or a urea derivative; and as necessary a nonionic detergent and/or sucrose. The kit may further include a solvent necessary to produce the reagent composition.

The term "kit" as used in the present specification refers to a package including a container (for example, a bottle, a plate, a tube, a dish, or the like) containing a particular material (for example, a constituent component). The kit is preferably provided with a manual for use of each material. Various forms of the verb "include" as used in the present specification to describe an aspect of the kit refer to a state in which the material is contained in any of the individual containers constituting the kit. A kit according to the present invention may be a single package containing a plurality of different compositions. The compositions may each be contained in one of a plurality of different containers in a case where the compositions are each in the form of a solution. A kit according to the present invention may include its constituent elements either (i) in a single container as the constituent elements are mixed with each other or (ii) in separate containers. The "manual" may be printed or written on a medium such as paper or an electronic medium such as a magnetic tape, a computer-readable disc or tape, or a CD-ROM. The manual shows a procedure for achieving the purpose of the kit. A kit according to the present invention may further include a container containing a diluent, a solvent, a cleaning fluid, or another reagent. In addition, a kit according to the present invention may include an instrument and a reagent that are necessary to carry out the procedure for achieving the purpose of the kit.

The term "light-transmitting property" as used in the present invention refers to (i) the proportion of transmitted light with respect to incident light or (ii) what proportion of fluorescence generated by excitation light irradiation passes through and how low scattering of the fluorescence light is. The expression "having an excellent light-transmitting property" means, as an example, that the proportion of outgoing light from an observation target (that is, transmitted light) is large with respect to light incident on the observation target. The light-transmitting property can be expressed as, for example, a percentage such that regarding the proportion of transmitted light with respect to incident light, (i) a substance that blocks light (for example, a black and thick plastic, a metal, or the like) has 0% and (ii) a transparent liquid such as water has 100%. For a biological material according to one embodiment having an excellent light-transmitting property, the proportion of transmitted light with respect to incident light is 40% or more, preferably 50% or more, 60% or more, 70% or more, 80% or more, 90% or more, 95% or more, 98% or more, or 99% or more in terms of light transmittance as measured with use of a spectrophotometer.

There is no particular limit to the procedure for preparing a reagent composition or reagent kit of the present invention with use of the composition or kit for producing the reagent composition. It is only necessary to dissolve each constituent component in a solvent. There is also no limit to the order in which the constituent components are dissolved in a solvent.

A biological material to which the present invention is to be applicated is not limited to any particular kind. Preferably, the biological material is a material derived from a plant or an animal, more preferably a material derived from an animal such as one selected from fish, amphibians, reptiles, birds, and mammals, particularly preferably a material derived from a mammal. The mammal is not limited to any particular kind and includes: laboratory animals such as mice, rats, rabbits, guinea pigs, and primates except for humans; pet animals such as dogs and cats; farm animals such as cows and horses; and humans.

Alternatively, the biological material may be an individual itself (except for a living human individual). Further alternatively, the biological material may be an organ, a tissue, a body fluid (for example, blood, saliva, blood serum, blood plasma, urine, synovial fluid, or spinal fluid), or a cell taken from an individual of a multicellular organism. The organism may be an adult or a fetus. A composition according to the present invention has excellent ability to make a subject transparent; therefore, even if the biological material is a tissue or organ (for example, the whole of or part of the brain, heart, lungs, liver, or kidneys) derived from a multicellular animal or an individual itself (for example, an embryo) of a multicellular animal which is not a human, the biological material can be subjected to a clearing treatment.

Further, the biological material may be either of (i) a material fixed for a microscopic observation and (ii) a non-fixed material. In a case of using a fixed material, the material is preferably immersed in, for example a 20% (v/w) sucrose-PBS solution, adequately (for example, for 24 hours or more) after being subjected to a fixing process. Furthermore, this material is preferably embedded into an OCT compound and frozen with liquid nitrogen, thawed in PBS, and then fixed again by a 4% (v/w) paraformaldehyde-PBS solution. The unit "% (w/v)" refers to a percentage of the weight (w (grams)) of a solvent to be used (sucrose or paraformaldehyde) to the volume (v (milliliters)) of the solution.

Specific examples of the biological material may be: a biological tissue having a fluorescent chemical substance injected therein; a biological tissue stained with a fluorescent chemical substance; a biological tissue having a fluorescent protein-expressed cell transplanted therein; and a biological tissue taken from a genetically-modified animal in which a fluorescent protein is expressed.

The present invention can significantly improve the light-transmitting property of a biological material, and can thus be combined with the latest microscopic techniques to allow high-throughput tissue imaging. Specifically, the present invention:

minimizes quenching of signals of a fluorescent protein or fluorescent substance;

allows multiple samples (several tens to several hundreds of samples) to be treated simultaneously in parallel;

makes a subject so highly transparent that the subject can be observed under a light-sheet microscope in combination; and minimizes the influence on the structuring of a tissue region.

Further, the present invention can significantly improve the light-transmitting property of a body fluid, and thus makes it possible to carry out an analysis that is free from the influence of a pigment in a body fluid.

[a. Aminoalcohol]

An aminoalcohol is a compound containing a hydroxyl group and an amino group. An aminoalcohol, which is well-known to be used as a neutralizer for an aqueous paint, is also used as an ingredient of an ink composition or pharmaceutical composition. Japanese Patent Application Publication, Tokukai, No. 2011-12226 A, for example, discloses an ink composition for ink jet printing which ink composition is produced by containing an aminoalcohol as a dispersion stabilizer. Japanese Patent Application Publication, Tokukai, No. 2009-221252 A discloses that containing an aminoalcohol in an ink composition allows the resulting ink to be wiped off easily.

A Scale reagent does not contain an aminoalcohol. Further, an aminoalcohol is neither a water-soluble polymer compound (that is, a compound that has a molecular weight of, for example, not less than approximately 50,000 to 60,000 and that substantially does not enter a cell) as an optional component of a Scale reagent nor a drying inhibition component such as glycerol as an optional component of a Scale reagent. The respective compositions disclosed in Japanese Patent Application Publication, Tokukai, No. 2011-12226 A and Japanese Patent Application Publication, Tokukai, No. 2009-221252 A both mentioned above each contain a polyhydric alcohol such as glycerin (glycerol) together with an aminoalcohol in view of preventing drying and provide wetness. This indicates that although an aminoalcohol and glycerin are both alcohols, they have respective functions different from each other and are not complementary to each other and that an aminoalcohol and glycerin may be used in combination, but are not interchangeable. This is fully recognized by persons skilled in the art.

As described above, an aminoalcohol is not disclosed or suggested as the composition of a Scale reagent, and in addition, not used in any publicly known clearing reagent. Persons skilled in the art thus cannot easily arrive at using an aminoalcohol in a reagent for preparing a biological material having an excellent light-transmitting property.

The aminoalcohol for use in the present invention may be an alkanolamine (methanolamine, ethanolamine, propanolamine, butanolamine, or the like) or an aromatic aminoalcohol, and is not limited to any of a primary alcohol, a secondary alcohol, or a tertiary alcohol. Examples of the aminoalcohol suitably usable for the present invention include monoethanolamine, diethanolamine, triethanolamine, monopropanolamine, dipropanolamine, tripropanolamine, monoisopropanolamine, diisopropanolamine, triisopropanolamine, methylethanolamine, dimethylethanolamine, trimethylethanolamine, ethylethanolamine, diethylethanolamine, triethylethanolamine, propylethanolamine, dipropylethanolamine, tripropylethanolamine, butylethanolamine, dibutylethanolamine, tributylethanolamine, methyldiethanolamine, ethyldiethanolamine, propyldiethanolamine, butyldiethanolamine, 2-amino-1-propanol, 2-amino-2-methyl-1-propanol, 2-amino-1,3-propanediol, 2-amino-2-ethyl-1,3-propanediol, 3-amino-1,2-propanediol, and 3-methylamino-1,2-propanediol. Additionally, the present invention may suitably use, for example, N,N,N',N'-tetrakis(1-hydroxyethyl)ethylenediamine, N,N,N',N'-tetrakis(2-hydroxyethyl)ethylenediamine, N,N,N',N'-tetrakis(1-hydroxypropyl)ethylenediamine, or N,N,N',N'-tetrakis(2-hydroxyprotyl)ethylenediamine.

In one embodiment, the aminoalcohol is preferably N,N,N',N'-tetrakis(2-hydroxypropyl)ethylenediamine, triethanolamine, triisopropanolamine, 2-amino-1,3-propanediol, 3-methylamino-1,2-propanediol, 3-amino-1,2-propanediol, or N,N,N',N'-tetrakis(2-hydroxyethyl)ethylenediamine. In a case where a reagent composition of the present invention is used for observation a fluorescent protein such as a GFP, the aminoalcohol is preferably N,N,N',N'-tetrakis(2-hydroxypropyl)ethylenediamine, triethanolamine, triisopropanolamine, or 2-amino-1,3-propanediol. In further view of cost and safety, the aminoalcohol is preferably N,N,N',N'-tetrakis(2-hydroxypropyl)ethylenediamine, triethanolamine, or triisopropanolamine, more preferably N,N,N',N'-tetrakis(2-hydroxypropyl)ethylenediamine or triethanolamine (that is, 2,2',2''-nitrilotriethanol).

[b. Urea or Urea Derivative]

The expression "urea or a urea derivative" as used in the present specification refers to at least one of urea and various urea derivatives, and is interchangeable with the expression "at least one compound selected from the group consisting of urea and urea derivatives".

The urea derivative is not limited to any particular kind. Specifically, the urea derivative is, for example, any of various kinds of ureine or compounds represented by General Formula (1) below. Note that the compounds represented by General Formula (1) include part of ureines.

[Chem. 1]

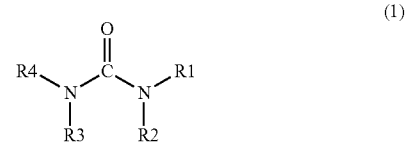

In a urea derivative represented by General Formula (1), each of R1, R2, R3, and R4 is independently a hydrogen atom (note that a urea compound in which all of R1 to R4 are hydrogen atoms is excluded, since it corresponds to urea), a halogen atom, or a hydrocarbon group. Further, in a case where the hydrocarbon group has a plurality of carbon atoms, part of the carbon atoms may be substituted by a hetero atom such as a nitrogen atom, an oxygen atom, or a sulfur atom. Examples of the hydrocarbon group encompass a chain hydrocarbon group and a cyclic hydrocarbon group.

Examples of the chain hydrocarbon group encompass a chain alkyl group, a chain alkenyl group, and a chain alkynyl group. The chain hydrocarbon group may have any number of carbon atoms. For example, the chain hydrocarbon group may be a linear or branched hydrocarbon group having 6 or fewer carbon atoms, preferably, an alkyl group having 1 to 3 carbon atoms. The chain hydrocarbon group may have a substituent group such as a halogen atom. Examples of the chain alkyl group encompass a methyl group, an ethyl group, a propyl group, an isopropyl group, a butyl group, an iso-butyl group, a sec-butyl group, a tert-butyl group, a hexyl group, and an octyl group.

The cyclic hydrocarbon group is, for example, a cycloalkyl group or a cycloalkenyl group. The cyclic hydrocarbon group may have a substituent group such as a halogen atom. Examples of the cycloalkyl group encompass a cycloalkyl group having 3 or more and preferably not more than 6 carbon atoms, such as a cyclopropyl group, a cyclobutyl group, a cyclopentyl group, or a cyclohexyl group. Examples of the cycloalkenyl group encompass a cycloalkenyl group having 3 or more and preferably not more than 6 carbon atoms, such as a cyclohexenyl group.

Examples of the halogen atom encompass a fluorine atom, a chlorine atom, a bromine atom, and an iodine atom.

The following 1) and 2) are more preferable, specific examples of the urea derivatives represented by General Formula 1.

1) Any three groups selected from R1 to R4 are hydrogen atoms, and the other one group is a halogen atom or a chain hydrocarbon group having 1 to 6 or less carbon atoms, more preferably, the other one group is an alkyl group having 1 to 3 carbon atoms or 1 or 2 carbon atoms.

2) Any two groups selected from R1 to R4 are hydrogen atoms, and each of the other two groups is independently a halogen atom or a chain hydrocarbon group having 1 to 6 or less carbon atoms, more preferably, each of the other two groups is an alkyl group having 1 to 3 carbon atoms or 1 or 2 carbon atoms. Even more preferably, one of the two groups which are hydrogen atoms is selected from R1 and R2, and the other of the two groups is selected from R3 and R4.

Urea is a component derived from a living organism and having extremely low toxicity. Thus, a reagent composition according to the present invention may, as with a Scale reagent, be used to make not only a fixed biological material transparent but also a non-fixed (living) biological material transparent. Further, urea causes only relatively small damage to a fluorescent protein and relatively small quenching of fluorescence signals of the fluorescent protein. Thus, a reagent composition according to the present invention may, as with a Scale reagent, be used for observation of a biological material with use of a fluorescent protein. In addition, urea is extremely inexpensive, extremely easily available, and extremely easy to handle. The reagent composition thus provides an extremely low-cost clearing treatment performed through a simple procedure.

In addition to the above advantages, a reagent composition according to the present invention can, as with a Scale reagent, remarkably improve the transparency of an opaque biological material having a high light scattering property, as compared to conventional clearing reagents. The reagent composition thus allows observation of various fluorescent proteins and fluorescent molecules present in ultra-deep tissues. For brain tissues in particular, the reagent composition makes it possible to make transparent a white matter layer, which has been a barrier to observation of deep parts, and thus allows observation of a region (for example, corpus callosum) located deeper than the white matter layer. Further, a clearing treatment that uses a reagent composition according to the present invention is reversible to a certain extent as with a case of using a Scale reagent. Specifically, simply immersing, in an equilibrated salt solution, a biological material that has been subjected to the clearing treatment releases the biological material from a clearing state, so that the non-transparent biological material can be preserved or used in, for example, an immunohistochemical assay or biochemical assay. Specific examples of the balanced salt solution include a balanced salt solution (for example, a PBS or HBSS) buffered with a phosphate; a balanced salt solution (TBS) buffered with tris hydrochloride; a population cerebrospinal fluid (ACSF); and a cell-culture basal medium such as MEM, DMEM, and Ham's F-12. The antigenicity of a protein or the like remains unchanged (preserved) before and after the clearing treatment. This makes it possible to perform analyses with use of a normal tissue-staining technique or immunostaining technique.

Note that using the above-described urea derivative instead of urea also provides similar effects.

The reagent composition according to the present invention is, as with a Scale reagent, not particularly limited in terms of the "urea" content as long as the clearing treatment for a biological material proceeds. The upper limit of the "urea" content is determined by the solubility of the urea to a solvent used. Although depending on the kind of a biological material to be subjected to the clearing treatment, a necessary clearing treatment can be performed, for instance, as follows: The treatment is performed for a long time period in a case where the reagent composition according to the present invention has a relatively small urea content, whereas the treatment is performed for a short time period in a case where the reagent composition according to the present invention has a relatively large urea content. In order to perform a clearing treatment to various degrees, the reagent composition contains urea at a concentration preferably within a range of 1 M or more and not more than 8.5 M, more preferably within a range of 3.5 M or more and not more than 8.5 M, particularly preferably within a range of 4 M or more and not more than 8 M. In a case where urea is replaced with a urea derivative (or a mixture of urea and a urea derivative), the content can be set within the same range as that for urea.

[c. Nonionic Detergent]

A nonionic detergent may also be used to produce a reagent composition for preparing a biological material having an excellent light-transmitting property. The resulting reagent composition is extremely useful in removing a light scattering substance from a biological material.

Examples of the nonionic detergent encompass: fatty acid detergents such as polyoxyethylene sorbitan monolaurate, polyoxyethylene sorbitan monopalmitate, polyoxyethylene sorbitan monostearate, and polyoxyethylene sorbitan monooleate; higher alcohol detergents such as polyvinyl alcohol; and alkylphenol detergents such as polyoxyethylene octylphenyl ether. Specifically, the detergent may be, for example, at least one selected from the group consisting of: Triton X (registered trademark) series such as Triton X-100 and Triton X-140; Tween (registered trademark) series such as Tween-20, Tween-40, Tween-60, and Tween-80; and NP-40 (product name). As the nonionic detergent, a mixture of two or more kinds may be used as necessary.

The nonionic detergent is contained in the reagent composition according to the present invention not containing sucrose (referred to also as "first reagent") in any amount that is 5 weight % or more, preferably within a range of 6 weight % or more and not more than 25 weight %, more preferably within a range of 8 weight % or more and not more than 20 weight %, even more preferably within a range of 10 weight % or more and not more than 20 weight %, particularly preferably within a range of 12 weight % or more and not more than 20 weight %. The unit "weight %" refers to a percentage of the weight (w (grams)) of a detergent to be used to the weight (w (grams)) of the reagent composition.

A detergent is an optional component of a Scale reagent. A Scale reagent preferably contains a detergent in a case where a clearing treatment is performed on a biological material on which a clearing treatment is relatively difficult. Further, a reagent may contain a nonionic detergent as necessary since a nonionic detergent gently facilitates entry of a Scale reagent into a biological tissue. The content of such a nonionic detergent is, however, mainly within a range of 0.05 weight % or more and not more than 0.2 weight %, and differs largely from the content of the nonionic detergent for use in the reagent composition according to the present invention.

A nonionic detergent, which gently facilitates entry of the present reagent into a biological tissue, may be contained as an optional component in the reagent composition according to the present invention (referred to also as "second solution") containing sucrose. The nonionic detergent is contained in the reagent composition according to the present invention in an amount preferably within a range of 0.025 weight % or more and not more than 5 weight %, more preferably within a range of 0.05 weight % or more and not more than 0.5 weight %, particularly preferably within a range of 0.05 weight % or more and not more than 0.2 weight %.

[d. Sucrose]

Sucrose may also be used to produce a reagent composition for preparing a biological material having an excellent light-transmitting property. Sucrose is extremely useful in producing a reagent having a refractive index suitable for the refractive index of a biological material to be applied. While the present specification mentions sucrose only, the present invention can use any substance having a refractive index adjusting effect similar to that of sucrose.

In this technical field, sucrose is typically used to replace a tissue fixing solution (for example, a paraformaldehyde solution) to prevent damage to fixed tissue. The concentration of sucrose is normally within a range of 10 weight % or more and not more than 30 weight %. The sucrose-containing reagent composition according to the present invention (referred to also as "second solution") is used preferably not to replace a tissue fixing solution, but after fixed tissue is replaced with sucrose, more preferably as the second solution after fixed tissue is replaced with sucrose and then the first solution according to the present invention is used.

Sucrose is contained in the sucrose-containing reagent composition according to the present invention (referred to also as "second reagent") in any amount that is 30 weight % or more, preferably within a range of 30 weight % or more and not more than 80 weight %, more preferably within a range of 30 weight % or more and not more than 70 weight %, even more preferably within a range of 40 weight % or more and not more than 70 weight %, particularly preferably within a range of 40 weight % or more and not more than 60 weight %. The unit "weight %" refers to a percentage of the weight (w (grams)) of sucrose in the second reagent with respect to the weight (w (grams)) of the second reagent.

[e. Solvent]

The solvent for use in the reagent composition according to the present invention is not limited to any particular kind, as long as the solvent allows the above-described active ingredients to be dissolved therein. Preferably, water is used as a main solvent; particularly preferably, only water is used as the solvent. Note that, in the present invention, what is meant by the expression "water is used as a main solvent" is that the volumetric percentage of water with respect to all solvents used is larger than that of any other solvent, and preferably that water is used in an amount that accounts for more than 50% and not more than 100% of the total volume of all solvents used. A reagent composition according to the present invention which reagent composition is prepared with use of water as a main solvent is referred to as a "reagent in the form of an aqueous solution".

In the case where water is used as a main solvent, dimethyl sulfoxide (DMSO) may be mixed with the water for application to a fixed sample, for example. It is expected that, for example, use of a mixture of DMSO and water to a fixed sample provides effects such as (i) improvement in permeability of the clearing reagent with respect to a biological material and (ii) facilitation of a clearing treatment with respect to a tissue having a keratin surface.

Main advantages of the use of water as the solvent are as follows:

1) The active ingredients of a reagent composition according to the present invention are excellent in solubility in water; therefore, the use of water as the solvent makes it possible to (i) inexpensively prepare the reagent composition according to the present invention and (ii) easily prepare the reagent composition according to the present invention.

2) Compared with a case where an organic solvent is used as a main solvent, the use of water as the solvent does not involve dehydration of a biological material when the biological material is subjected to a clearing treatment; therefore, the use of water as the solvent can prevent the problem of shrinkage of a biological material.

3) Compared with a case where an organic solvent is used as a main solvent, the use of water as the solvent significantly reduces the possibility of damaging a fluorescent protein; this makes it possible to observe, with use of a fluorescent protein, a biological material having been subjected to a clearing treatment.

4) The use of water as the solvent makes it possible to apply the reagent composition according to the present invention not only to a clearing treatment on a fixed material but also to a clearing treatment on a living material.

5) The use of water as the solvent makes a clearing treatment reversible (described later), that is, the use of water as the solvent can as necessary bring a biological sample having been subjected to a clearing treatment back to a state that it had before the clearing treatment.

6) Compared with a case where an organic solvent is used as a main solvent, the use of water as the solvent enhances safety in handling of the reagent composition according to the present invention.

A reagent composition according to the present invention may be a buffer solution that can maintain a pH suitable for a biological material to be subjected to a clearing treatment. Further, a reagent composition according to the present invention may have an osmotic pressure adjusted to such a degree that no deformation is caused of a biological material to be subjected to a clearing treatment and that the active ingredients sufficiently penetrate into the biological material.

[f. Other Optional Components]

A reagent composition according to the present invention can, as with a Scale reagent, contain a "drying inhibition component" as necessary, which is at least one compound selected from glycerol, carboxy vinyl polymer, hydroxypropyl methylcellulose, propylene glycol, and macrogol. The drying inhibition component prevents drying of a biological material subjected to a clearing treatment. In particular, in a case where the biological material after the cleaning treatment may be kept waited for a relatively long time period before an optical microscopic observation thereof, or in a case where an optical microscopic observation of the biological material takes a long time, the reagent composition according to the present invention preferably contains any of the above drying inhibition components.

In the case where the "drying inhibition component" such as glycerol is used, its content is not particularly limited, preferably at a concentration within a range of 2.5 weight % or more and not more than 20 weight %, more preferably at a concentration within a range of 5 weight % or more and not more than 15 weight %, particularly preferably at a concentration within a range of 8 weight % or more and not more than 12 weight %. The unit "weight %" refers to a percentage of the weight (w (grams)) of the "drying inhibition component" to be used with respect to the weight (w (grams)) of the reagent composition.

A reagent composition according to the present invention may, as with a Scale reagent, contain an additive such as a pH adjusting agent and an osmotic pressure controlling agent as necessary in addition to the above ingredients.

[2. Method According to Present Invention]

To prepare a biological material having an excellent light-transmitting property, a first solution is prepared that includes urea or a urea derivative, an aminoalcohol, and a nonionic detergent. A biological material is placed in the prepared first solution so that the first solution is permeated into the biological material. The biological material into which the first solution is to be permeated is preferably fixed with use of a paraformaldehyde solution and then replaced with a sucrose solution in advance.

The first solution may be prepared with use of a kit for producing a reagent composition according to the present invention, or may be provided by itself as a reagent composition according to the present invention. A method according to the present invention is, in other words, characterized by including a step (that is, a first permeating step) of causing a first solution containing urea or a urea derivative, an aminoalcohol, and a nonionic detergent to permeate a biological material for preparation of a biological material having an excellent light-transmitting property. A biological material into which the first solution has been permeated exhibits a light-transmitting property superior to that brought about through any of the effects produced by conventionally publicly known clearing reagents. This indicates that the first solution has removed a light scattering substance (mainly lipids) from the biological material. The first solution, as described above, exhibits an excellent effect of making transparent an organ or tissue that contains lipids in a large amount.

Blood mixed with the first solution has a significantly improved light-transmitting property. This indicates that the first solution has removed pigments (mainly hemoglobins) from the blood. The first solution, as described above, exhibits an unpredictable, excellent effect of making transparent (i) blood and (ii) an organ or tissue that contains blood in a large amount.

A method according to the present invention preferably includes permeation of a second solution into a biological material (that is, a second permeating step) in addition to the first permeating step. In this case, a second solution is prepared that includes urea or a urea derivative, an aminoalcohol, and sucrose. A biological material is placed in the prepared second solution so that the second solution is permeated into the biological material. The biological material into which the second solution is to be permeated is preferably fixed with use of a paraformaldehyde solution and then replaced with a sucrose solution in advance, more preferably additionally washed to sufficiently remove the first solution after the first permeating step. A biological material into which the second solution has been permeated exhibits a light-transmitting property comparable to that brought about through any of the effects produced by conventionally publicly known clearing reagents. A biological material having been subjected to both the first permeating step and the second permeating step exhibits a light-transmitting property incomparably superior to that brought about through any of the effects produced by conventionally publicly known clearing reagents. This indicates that there remains a light scattering substance that cannot be removed with use of the first solution and that the second solution has removed such a remaining light scattering substance or reduced light scattering by the biological material after the first permeating step. Further, the second permeating step causes the biological material swollen due to the first permeating step to return to its original size. The second solution, as described above, significantly enhances the excellent effect of the first solution of making transparent an organ or tissue that contains lipids in a large amount.

In one embodiment, a method according to the present invention is preferably applied through the following procedure:

1) Extract the brain from a mouse fixed by perfusion fixation involving use of a 4% paraformaldehyde solution, and fix the extracted brain for 12 to 24 hours in a paraformaldehyde solution.

2) Cause the fixed brain to undergo a replacement in a 20% sucrose-PBS solution.

3) Cause the brain having undergone the replacement to undergo another replacement in the first solution.

4) Wash the brain, into which the first solution has been permeated, with PBS several times each for several hours.

5) Cause the washed brain to undergo another replacement in the second solution.

6) Observe the brain, into which the second solution has been permeated, or preserve the brain after it was washed with PBS.

A biological material prepared with use of N,N,N',N'-tetrakis(2-hydroxypropyl)ethylenediamine as the first solution had a particularly excellent light-transmitting property. A biological material prepared with combinational use of triethanolamine (that is, 2,2',2"-nitrilotriethanol) as the second solution had a further improved light-transmitting property. In a case where these aminoalcohols are used, quenching of fluorescence signals of a fluorescent protein such as a GFP is extremely small. Thus, whole brain imaging suitably uses the biological material.

In a case where an immunohistochemical assay is performed with use of a method according to the present invention, the immunohistochemical assay is preferably performed between the steps 4) and 5). When to perform an immunohistochemical assay is, however, not limited to that stage.

The temperature at which the above procedure (clearing treatment) is carried out is not particularly limited, but is preferably within a range of 15° C. or higher and 45° C. or lower. The processing time period for which the clearing treatment is performed is not particularly limited, but is preferably within a range of 2 hours or longer and 6 months or shorter, more preferably within a range of 12 hours or longer and 7 days or shorter.

Further, the present invention provides a biological material having an excellent light-transmitting property to be prepared according to a method of the present invention. A Scale method provides good light transmittance that allows observation through a two-photon microscope is achieved with use of a mouse brain slice having a thickness of not more than 100 µm. In contrast, a biological material (whole brain) prepared by a method of the present invention produces a particularly excellent effect, that is, a transmittance of 60% or more with respect to light having a wavelength of not less than 520 nm, a transmittance of 70% or more with respect to light having a wavelength of not less than 560 nm, and a transmittance of 80% or more with respect to light having a wavelength of not less than 640 nm as demonstrated in the Examples described later, only after the first permeating step. In addition, combining the first permeating step with the second permeating step allows the transmittance to be improved further at parts where scattering is large. The present invention can, as described above, impart an excellent light-transmitting property such as the above to a biological material that is not a slice, and therefore allows a resulting biological material to be observed through a single-photon confocal microscope.

A biological material having an excellent light-transmitting property which biological material has been prepared by a method of the present invention is suitably observed with use of light having a wavelength of not less than 520 nm. The present invention provides a biological material having an excellent light-transmitting property with respect to light having the color of, for example, red (wavelength region of 740 to 625 nm), orange (wavelength region of 625 to 590 nm), yellow (wavelength region of 590 to 565 nm), or green (wavelength region of 565 to 520 nm) within the visible-light range.

[3. Further Use of Present Invention]

On a biological material having been subjected to the clearing treatment, an observation step with use of, for example, an optical microscope is subsequently performed. On a biological material to be subjected to the observation step, a visualizing treatment step such as staining or marking may as necessary be performed (i) before the clearing treatment step or (ii) after the clearing treatment step and before the observation step.

For example, in a case where the visualizing treatment step involves use of a fluorescent protein, a fluorescent protein gene is introduced into a living biological material before the clearing treatment step so that the fluorescent protein will be expressed therein.

In a case where the visualizing treatment step is (i) injection of fluorescent chemical (small) molecules (which is not a fluorescent protein) into a biological material or (ii) staining of a biological material with use of fluorescent chemical (small) molecules, the visualizing treatment step is preferably performed before or during the clearing treatment step. However, the visualizing treatment step may be performed after the clearing treatment step. Alternatively, the visualizing treatment step may be staining of a biological material with use of a chemical substance which is not fluorescent chemical molecules.

The observation step can be performed with use of any type of optical microscope. For example, the observation step can be performed by employing a three-dimensional super-resolution microscopy technique (for example, STED, 3D PALM, FPALM, 3D STORM, or SIM). The observation step may be performed by employing a multiphoton excitation type (typically, two-photon excitation type) optical microscopy technique preferably with use of a single-photon confocal microscope or light-sheet macro-zoom microscope.

As demonstrated in the Examples described later, the use of the present invention allows a three-dimensional immunohistochemical. The present invention, which is advantageous as such, is extremely useful as a tool for analysis of autoimmune diseases. In the case where the present invention is used for analysis of autoimmune diseases, the organism that provides a biological material may be an adult or an embryo. The organism is preferably a mammal. Preferable examples of the mammal include: primates excluding humans (for example, marmosets); and humans. The biological material may be an individual itself (except for a living human individual), but a tissue or organ derived from a multicellular animal (for example, the whole of or part of the brain) is suitably used for the present invention.

Autoimmune diseases are diseases that develop in cases where the immune system produces an antibody (autoantibody) against self (endogenous antigen) and reacts to eliminate the endogenous antigen, which is recognized as nonself. A large number of autoimmune diseases have been discovered to date, and a lot of research has been conducted on autoimmune diseases. It is, however, still difficult to learn what site of tissues of a patient the autoantibody actually reacts with. It is thus difficult to identify the focus responsible for an autoimmune disease. Further, it is difficult to learn what specific antigen against the autoantibody produced.

In one embodiment, the present invention provides a method for searching for a tissue site reactive with an autoantibody through the immunohistochemical assay. Such a tissue site may be the focus responsible for a disease caused by an autoantibody. In another embodiment, the present invention provides a method for searching, through the immunohistochemical assay, for an antigen against an autoantibody.

The use of the present invention allows confirmation of an antigen-antibody reaction in a state where a complicated structure of the biological tissue is maintained. The present invention thus makes it possible to search for what site of tissues of a body an autoantibody actually reacts with and to search for the antigen against an autoantibody produced. For instance, an autoantibody that is collected from an autoimmune disease patient and that is fluorescence-labeled can be subjected to the visualizing treatment step and then to the observation step to find a site that reacts with the autoantibody and thus to find the antigen against the autoantibody.

Identifying the focus responsible for a disease makes it possible to discover relationships to various central nerve diseases (including psychiatric disorders, sleep disorders, and neurodegenerative diseases). For instance, by confirming the reactivities of autoantibodies with biological materials derived from model animals having various central nerve diseases, it is possible to obtain data that allows various pathologies to be elucidated from the viewpoint of autoimmune diseases.

A biological material having been subjected to the clearing treatment may then be subjected to, for example, a biochemical assay. A biochemical assay is an assay for chemically analyzing, for example, proteins, lipids, or low-molecular compounds contained in a biomaterial such as a cell or a tissue. A biochemical assay is used as, for example, the simplest and most useful information gathering means in clinical floors. The results of the analysis are used in, for example, diagnosis or determination of prognosis of various diseases (for example, liver diseases, kidney diseases, diabetes, hypertension, heart diseases, and hyperuricemia).

Typically, a biochemical assay is achieved by separating out, for example, proteins, lipids, or low-molecular compounds contained in a biomaterial by chromatography, electrophoresis, or the like and detecting such proteins, lipids, or low-molecular compounds through an antigen-antibody reaction or with use of a special detector (such as a mass spectrometer). Combination with such a biochemical assay allows a composite analysis of a sample having been subjected to a clearing treatment. A biological material to which the present invention has been applied is thus preferably subjected to a biochemical assay. A biological material to be subjected to a biochemical assay may as necessary be stained or fluorescence-labeled as desired in advance.

In one embodiment, the present invention provides an integrated analysis environment combined with a method for biochemically analyzing components of a biological material on the basis of the biochemical assay. A biological material suitably used for the present invention may be an organ or tissue (for example, the brain, heart, lungs, kidneys, or liver) or a body fluid (for example, blood, saliva, blood serum, blood plasma, urine, synovial fluid, or spinal fluid) obtained from an individual. The present invention may be employed in various publicly known biochemical analyses. For instance, in a case where an imaging analysis subsequent to a clearing treatment has found a site that requires a further analysis, the present invention is suitably used in, for example, proteomics analysis of that site (for example, an analysis involving use of a mass spectrometer). Examples of the target of the measurement include, but are not limited to, proteins, nucleic acids, lipids, sugars, and in vivo low-molecular compounds.

Examples

The following will further specifically describe the present invention with reference to the Examples below. The present invention is, however, not limited to the Examples.

[1. Light-Transmitting Property of Whole Mouse Brain after Clearing Treatment]

A 6-month-old individual was perfused with a room-temperature PBS from the left ventricle of the heart with use of a peristaltic pump. Then, the individual was perfused with a room-temperature fixing solution (4% paraformaldehyde-PBS, pH of 7 to 8). This systemically and completely fixed the mouse.

Subsequently, the cranial bones were removed from the mouse, and the whole brain was carefully taken out therefrom. Then, the whole brain taken out was immersed in an ice-cold fixing solution (4% paraformaldehyde-PBS, pH of 7 to 8) overnight at 4° C. Thereafter, the fixed whole brain was transferred into a 20% sucrose-PBS solution, and was then permeated with the 20% sucrose-PBS solution at 4° C. (a) of FIG. 1 shows an optical micrograph of the brain sample (sample a) into which the 20% sucrose-PBS solution had been permeated. The light transmittance of the sample a (central portion of the sample) was measured with use of Konica Minolta CM-5 spectrophotometer (see (d) of FIG. 1).

The brain replaced by the 20% sucrose-PBS solution was transferred into the first solution (Sol. PE) including 25% N,N,N',N'-tetrakis(2-hydroxypropyl)ethylenediamine, 15% Triton X-100 (Nacalai Tesque, Cat No. 25987-85), and 25% urea. The first solution was permeated into the brain for 7 days at 37° C. while the brain was gently shaken. This caused the brain to undergo a replacement in the first solution. (b) of FIG. 1 shows an optical micrograph of the brain sample (sample b) into which the first solution had been permeated. The light transmittance of the sample b (central portion of the sample) was measured with use of Konica Minolta CM-5 spectrophotometer. (see (d) of FIG. 1). Subsequently, the brain having undergone a replacement in the first solution was transferred into PBS, and was gently shaken at room temperature 2 to 3 times each for 3 to 12 hours to be washed. The washed brain was transferred into the second solution including 10% triethanolamine, 0.1% Triton X-100, 25% urea, and 50% sucrose, and was gently shaken at room temperature for 4 days or longer, so that the brain underwent a replacement in the second solution. (c) of FIG. 1 shows an optical micrograph of the brain sample (sample c) into which the second solution had been permeated. The light transmittance of the sample c (central portion of the sample) was measured with use of Konica Minolta CM-5 spectrophotometer (see (d) of FIG. 1).

The sample a had a poor light-transmitting property at any wavelength region. The sample b had a greatly improved light-transmitting property. Comparison between the sample b and the sample c proves that the replacement with the second solution facilitated clearing of the white matter.

[2. Clearing and Scanning of Whole Brain]

A 7-month-old individual mouse knocked in with H2B-mCherry (histone H2B protein fused with fluorescent protein mCherry) at the ROSA 26 locus (Takaya Abe et al., "Establishment of Conditional Reporter Mouse Lines at ROSA 26 Locus For Live Cell Imaging" Genesis vol. 49: 579-590 (2011)) was perfused with a room-temperature PBS from the left ventricle of the heart with use of a peristaltic pump. Then, the individual mouse was perfused with a room-temperature fixing solution (4% paraformaldehyde-PBS, pH of 7 to 8). This systemically fixed the mouse.

Subsequently, the cranial bones were removed from the mouse, and the whole of the brain was carefully taken out therefrom. Then, the whole brain taken out was immersed in an ice-cold fixing solution (4% paraformaldehyde-PBS, pH of 7 to 8) overnight at 4° C. Thereafter, the fixed whole brain was transferred into a 20% sucrose-PBS solution, and was then permeated with the 20% sucrose-PBS solution at 4° C.

The brain having undergone a replacement in the 20% sucrose-PBS solution was transferred into the first solution (Sol. PE) including 25% N,N,N',N'-tetrakis(2-hydroxypropyl)ethylenediamine, 15% Triton X-100 (Nacalai Tesque, Cat No. 25987-85), and 25% urea. The first solution was permeated into the brain for 10 days at 37° C. This caused the brain to undergo a replacement in the first solution. The brain having undergone a replacement in the first solution was transferred into PBS, and was gently shaken at room temperature 2 to 3 times each for 3 to 12 hours to be washed.

The washed brain was transferred into the second solution (Sol. CL) including 10% triethanolamine, 0.1% Triton X-100, 25% urea, and 50% sucrose, and was gently shaken at room temperature for 4 days or longer, so that the brain underwent a replacement in the second solution. The brain having undergone a replacement in the second solution was used as a sample for observation.

The sample for observation was dipped in a mixed oil containing TSF4300 and a mineral oil at a ratio of 1:1, and was subjected to whole brain scanning involving use of a light-sheet macro-zoom microscope (LaVision, Ultramicroscope). The data obtained was used to form a three-dimensionally reconstructed image on Imaris (Bitplane) (see FIG. 2). (a) of FIG. 2 shows an image of the three-dimensionally reconstructed image as viewed from the ventral side of the sample brain. (b) shows a plane X-Y image image as observed with the microscope. (c) shows a coronal section of the three-dimensionally reconstructed image of the sample. (d) shows a sagittal section of the three-dimensionally reconstructed image of the sample. As shown, it has been proven that a tissue treated with use of the present invention has a light-transmitting property high enough for the tissue to be applied to a light-sheet macro-zoom microscope.

[3. Three-Dimensional Immunohistochemical Assay]

A 4-month-old individual mouse knocked in with H2B-EGFP (histone H2B protein fused with fluorescent protein EGFP) at the ROSA 26 site (Takaya Abe et al.; see above) was perfused with a room-temperature PBS from the left ventricle of the heart with use of a peristaltic pump. Then, the individual mouse was perfused with a room-temperature fixing solution (4% paraformaldehyde-PBS, pH of 7 to 8). This systemically fixed the mouse.

Subsequently, the cranial bones were removed from the mouse, and the whole brain was carefully taken out therefrom. Then, a brain region including the hypothalamus was cut out carefully. The brain region tissue cut out was immersed in an ice-cold fixing solution (4% paraformaldehyde-PBS, pH of 7 to 8) overnight at 4° C. Thereafter, the fixed tissue was transferred into a 20% sucrose-PBS solution, and the 20% sucrose-PBS solution was then permeated at 4° C.

The tissue having undergone a replacement in the 20% sucrose-PBS solution was transferred into the first solution (Sol. PE) including 25% N,N,N',N'-tetrakis(2-hydroxypropyl)ethylenediamine, 15% Triton X-100 (Nacalai Tesque, Cat No. 25987-85), and 25% urea. The brain was gently shaken for 24 hours at 4'C. This caused the tissue to undergo a replacement in the first solution. The tissue having undergone a replacement in the first solution was transferred into PBS, and was gently shaken at room temperature 2 to 3 times each for 3 to 12 hours to be washed.

The washed tissue was transferred into a diluent of an anti-Copeptin antibody (Santacruz) and an anti-VIP antibody (Immunostar) (1:100 and 1:300, respectively), and reacted for 3 days. The diluent was removed, and the tissue having reacted with the antibody was transferred into a 0.1% Triton X-100-PBS. The tissue was gently shaken at room temperature or 37° C. 2 to 3 times each for 3 to 12 hours to be washed.

The washed tissue was transferred into a diluent of a secondary antibody (1:1000) conjugated with Alexa fluorescent dye, and reacted for 3 days. The diluent was removed, and the tissue having reacted with the secondary antibody was then transferred into a 0.1% Triton X-100-PBS. The tissue was gently shaken at room temperature or 37° C. 2 to 3 times each for 3 to 12 hours to be washed. The tissue was further transferred into PBS, and was gently shaken at room temperature 1 to 2 times each for 3 to 12 hours to be washed.

The washed tissue was transferred into a 1% paraformaldehyde-PBS, and was shaken at room temperature for approximately 30 minutes to crosslink the antibody. The tissue was then transferred into PBS, and was gently shaken at room temperature 1 to 2 times each for 3 to 12 hours to be washed. Subsequently, the tissue was transferred into the second solution (Sol. CL) including 10% triethanolamine, 0.1% Triton X-100, 25% urea, and 50% sucrose, and was gently shaken at room temperature for 2 days or longer for a replacement with the second solution. The tissue having undergone a replacement in the second solution was used as a sample for observation.

A suprachiasmatic nucleus region of the sample for observation was observed through a confocal laser scanning microscope (LSM 700, Carl Zeiss) from the ventral side of the brain to a depth of approximately 500 μm. The data obtained was used to reconstruct a three-dimensional image with Imaris (Bitplane) (see FIG. 2).

(a) of FIG. 3 shows an image of the three-dimensionally reconstructed image of the sample as observed from obliquely above. (b) shows an image of the three-dimensionally reconstructed image of the sample as observed from a substantially horizontally lateral side. As shown, a three-dimensional image was successfully observed of not only a fluorescent image of an EGFP but also an immunostaining image of Copeptin and VIP.

[4. Effects for Blood]

0.1 mL of mouse blood fixed with paraformaldehyde was mixed with 0.4 mL of treatment solutions (PBS solution, the first solution (Sol. PE) containing 25% urea, or an aminoalcohol solution [aqueous solution containing 25% N,N,N', N'-tetrakis(2-hydroxypropyl)ethylenediamine]) was added. Immediately after the mixing at room temperature, they were centrifuged at 15000 rpm for 5 minutes. The supernatant was separated, and then 0.5 mL of the treatment solution was added to the precipitate. The mixed liquid was centrifuged again similarly to separate a precipitate from a supernatant. Such an operation to wash the precipitate was repeated three times, and then 0.5 mL of the treatment solution was mixed with the precipitate.

Figure 4:
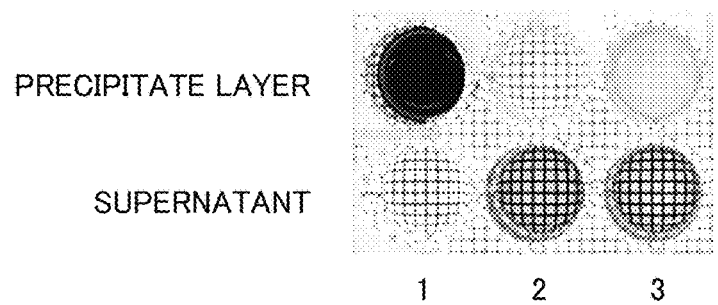
FIG. 4 is a figure according to an Example of the present invention which figure shows mouse blood treated with use of the present invention.

FIG. 4 shows the results. Columns 1 to 3 in FIG. 4 show supernatants and precipitates (blood corpuscle sediments) produced by centrifugation of the mixed liquid containing blood and the PBS, the mixed liquid containing blood and the first solution, and the mixed liquid containing blood and the aminoalcohol solution, respectively.

The results confirmed that treating blood with the first solution causes decoloration of the precipitates (see column 2). The results showed that this effect is attributed to the aminoalcohol contained in the first solution (see column 3).

[5. Clearing of Various Tissues]

A 4-month-old mouse individual that expressed fluorescent protein mKate2 was perfused with 10 mL of a heparin PBS solution from the left ventricle of the heart at room temperature with use of a peristaltic pump. Then, the mouse individual was perfused with 150 mL of a room-temperature fixing solution (4% paraformaldehyde-PBS, pH of 7 to 8). This systemically fixed the mouse. Subsequently, the mouse was washed with 20 mL of a PBS solution, and was then further perfused with 20 mL of a solution prepared by 2-fold dilution of the first solution.

Subsequently, the heart, lungs, kidneys, and liver were extracted from the fixed mouse. The tissues extracted were immersed in the first solution for 5 days, and were then immersed in the second solution for 4 days for a clearing treatment.

Figure 5:
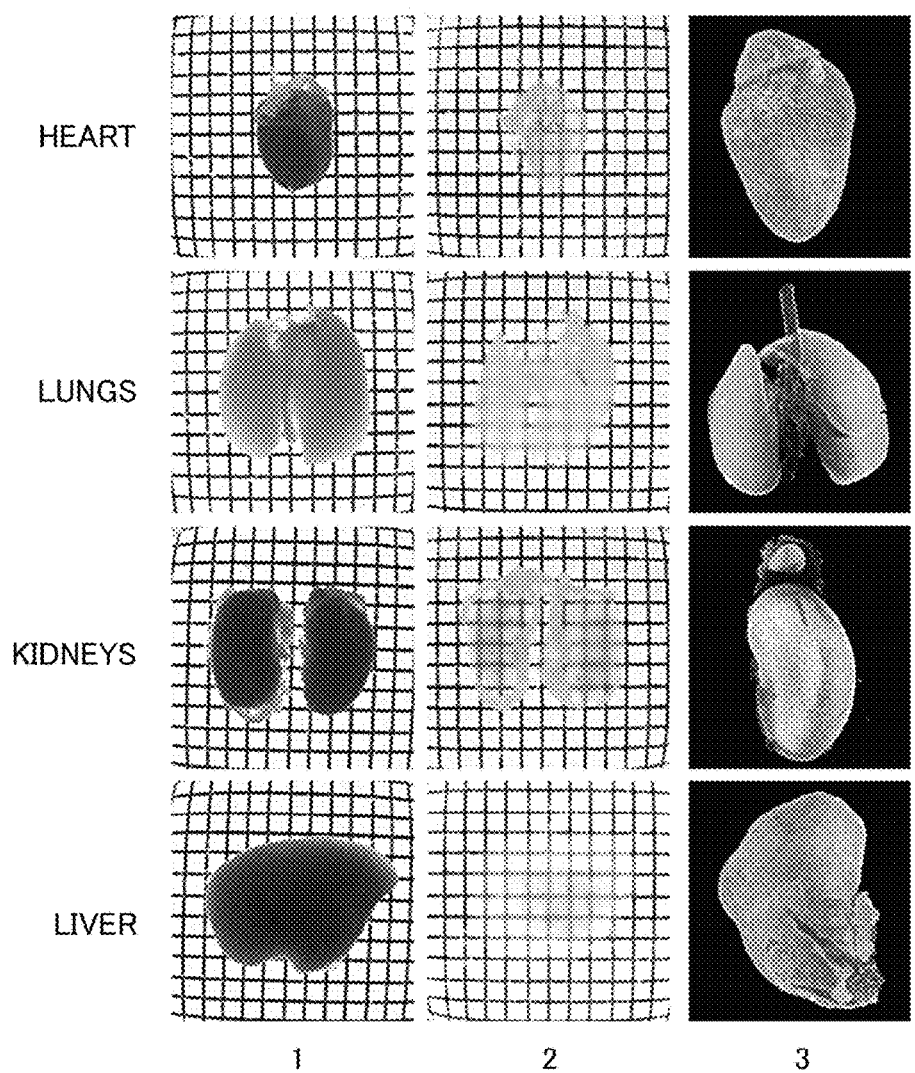
FIG. 5 is a figure according to an Example of the present invention which figure shows results of checking light-transmitting properties of various mouse tissues treated with use of the present invention and results of three-dimensional fluorescence imaging.

Columns 1 and 2 of FIG. 5 show optical micrographs of the tissue samples, which were taken before and after the clearing treatment. Further, tissue samples stained with cell nucleus staining reagent SYTO16 during the clearing treatment were used for three-dimensional imaging involving use of a light-sheet microscope so that the fluorescence of mKate2 (red) and the fluorescence of SYTO16 (green) were imaged together (see column 3).

The figure shows that a clearing treatment according to the present invention is applicable also to any of various tissues other than brain tissue as a biological material and that the biological material having been subjected to the clearing treatment has a light-transmitting property high enough to be applied to a light-sheet microscope.

As described above, the present invention has the following advantages:

[1] Can use a water-soluble reagent to make a biological material transparent at a level equivalent to that attained with use of a technique involving use of an organic solvent, and has allowed observation through a light-sheet microscope.

[2] Has minimized quenching of fluorescence signals in comparison to a technique involving use of an organic solvent, and improved safety dramatically.

[3] Usable in not only detection of a fluorescent protein but also in an immunohistochemical assay with an antibody or counterstain, for example, and has thus made a three-dimensional immunohistochemistry possible.

[4] Has modified and optimized the composition of the reagent through compound screening to clearly shorten the processing time period (from a period in months to a period in days or weeks) in comparison to a Scale method and to improve transparency from a level that requires a two-photon microscope to a level that allows use of a light-sheet macro microscope.

[5] Allows practical use at low costs because the compounds screened were all inexpensive.

[6] Has established a simple protocol that does not require specialized equipment or a complicated operation, and thus allowed multiple samples to be treated in parallel.

[7] Allows scanning of the whole brain to be completed in approximately 1 hour per color in a case where a light-sheet macro microscope is adapted, and thus allows a multicolor image to be obtained with almost no time lag and data of a three-dimensional image of the whole brain to be created.

[8] Allows an immunohistochemistry to be performed in a state where a complicated structure of the biological tissue is maintained three-dimensionally, and thus makes it possible to search for what site of tissues of a test subject an autoantibody actually reacts with and to search for the antigen against an autoantibody.

The present invention is not limited to the description of the embodiments and examples above, but may be altered by a skilled person within the scope of the claims. Any embodiment based on a proper combination of technical means disclosed in different embodiments is also encompassed in the technical scope of the present invention.

INDUSTRIAL APPLICABILITY

The present invention allows highly accurate imaging even with use of a general-purpose single-photon confocal microscope without the need to use a two-photon excitation type optical microscope. Further, when combined with the latest microscopic technique, for example, a light-sheet macro-zoom microscope, the present invention allows high-throughput tissue imaging. This will contribute greatly to not only an advance in the medical science but also, for example, development of new pharmaceuticals.

The invention claimed is:

1. A method for preparing a biological material having an excellent light-transmitting property,
the method comprising:
a first permeating step comprising contacting the biological material with a first solution for a period of time and at a concentration sufficient for permeating the first solution into the biological material and making the biological material having the excellent light-transmitting property,
wherein the first solution contains
polyhydric aminoalcohol;
urea; and
Triton X-100 having a concentration in the range of at least 10% by weight to 20% by weight; and
wherein the excellent light-transmitting property comprises a light transmitting property in which a proportion of transmitted light, with respect to incident light is 40% or more.

2. The method according to claim 1, further comprising
a second permeating step of permeating into a biological material a second solution containing:
an aminoalcohol;
urea; and
sucrose.

3. The method according to claim 2, wherein
the second solution further contains Polyethylene Glycol Mono-p-isooctylphenyl Ether.

4. A biological material having an excellent light-transmitting property, the biological material comprising
a biological material that has been permeated with a first solution comprising:
polyhydric aminoalcohol;
urea; and
Polyethylene Glycol Mono-p-isooctylphenyl Ether having a concentration in a range of at least 10% by weight to 20% by weight;
wherein the excellent light-transmitting property comprises a light transmitting property in which a proportion of transmitted light with respect to incident light is 40% or more.

5. The biological material of claim 4, wherein the biological material has been further permeated with a second solution comprising:
an aminoalcohol;
urea; and
sucrose.

6. The biological material of claim 5, wherein the second solution further comprises Polyethylene Glycol Mono-p-isooctylphenyl Ether.

* * * * *

UNITED STATES PATENT AND TRADEMARK OFFICE
CERTIFICATE OF CORRECTION

| | |
|---|---|
| PATENT NO. | : 10,267,714 B2 |
| APPLICATION NO. | : 14/911778 |
| DATED | : April 23, 2019 |
| INVENTOR(S) | : Etsuo Susaki, Hiroki Ueda and Kazuki Tainaka |

Page 1 of 1

It is certified that error appears in the above-identified patent and that said Letters Patent is hereby corrected as shown below:

In the Claims

Column 22, Line 4, cancel the text "Triton X-100" in Claim 1, and insert the following text in place thereof -- Polyethylene Glycol Mono-p-isooctylphenyl Ether --

Signed and Sealed this
Third Day of September, 2019

Andrei Iancu
*Director of the United States Patent and Trademark Office*